United States Patent
Yokoyama et al.

(10) Patent No.: US 8,979,761 B2
(45) Date of Patent: Mar. 17, 2015

(54) SLEEPINESS ASSESSMENT APPARATUS

(75) Inventors: Kiyoko Yokoyama, Anjo (JP); Issei Takahashi, Nagoya (JP); Hayato Ohashi, Nagoya (JP); Genki Tabata, Matsudo (JP)

(73) Assignee: Nagoya City University, Nagoya-shi (JP)

( * ) Notice: Subject to any disclaimer, the term of this patent is extended or adjusted under 35 U.S.C. 154(b) by 383 days.

(21) Appl. No.: 13/376,719

(22) PCT Filed: May 26, 2010

(86) PCT No.: PCT/JP2010/058904
§ 371 (c)(1),
(2), (4) Date: Dec. 7, 2011

(87) PCT Pub. No.: WO2010/143535
PCT Pub. Date: Dec. 16, 2010

(65) Prior Publication Data
US 2012/0078122 A1  Mar. 29, 2012

(30) Foreign Application Priority Data
Jun. 8, 2009  (JP) .................................. 2009-137551

(51) Int. Cl.
*A61B 5/0205* (2006.01)
*A61B 5/0245* (2006.01)
(Continued)

(52) U.S. Cl.
CPC ................. *A61B 5/18* (2013.01); *A61B 5/0245* (2013.01); *A61B 5/0816* (2013.01); *A61B 5/6887* (2013.01)
USPC ............ 600/484; 600/500; 600/509; 600/529

(58) Field of Classification Search
USPC .................................. 600/484, 529, 500, 509
See application file for complete search history.

(56) References Cited

U.S. PATENT DOCUMENTS 5,769,085 A * 6/1998 Kawakami et al. ........... 600/519
6,337,629 B1 * 1/2002 Bader ........................... 340/576
(Continued)

FOREIGN PATENT DOCUMENTS

JP        H026231 A   *  1/1990   ............... A61B 5/02
JP        A-4-183439      6/1992
(Continued)

OTHER PUBLICATIONS

Jan. 17, 2012 International Preliminary Report on Patentability issued in International Application No. PCT/JP2010/058904.
(Continued)

*Primary Examiner* — Navin Natnithithadha
*Assistant Examiner* — Meredith Weare
(74) *Attorney, Agent, or Firm* — Oliff PLC (57) ABSTRACT

A sleepiness assessment value P1 is set to be an average heart rate HR (S130). A sleepiness assessment value P2 is set to be a standard deviation σ of a respiration interval RespI for one minute (S150). A sleepiness assessment value P3 is set to be a value that is obtained by dividing, by one minute, an integrated value of a square of an average heartbeat interval RRIavg in a case where a variation in which a heartbeat interval RRI increases occurs (in a case where an RRI count value Xi is a value of one) (S190). A sleepiness assessment value P4 is set to a value that is obtained by averaging a variation ratio in a case where a variation in which the respiration interval RespI increases occurs (in a case where an RRI count value Yi is a value of one) (S210). A sleepiness assessment value P is set to be a value obtained by summing values that are obtained by multiplying the individual sleepiness assessment values P1 to P4 by weight coefficients a to d, each of which is set for a corresponding one of the sleepiness assessment values P1 to P4 (S220). When the sleepiness assessment value P is smaller than a value of zero, it is determined that a person is highly alert (S240), and, when the sleepiness assessment value P is equal to or larger than the value of zero, it is determined that the person is less alert (S250).

6 Claims, 5 Drawing Sheets

(51) Int. Cl.
*A61B 5/08* (2006.01)
*A61B 5/18* (2006.01)
*A61B 5/00* (2006.01)

(56) References Cited

U.S. PATENT DOCUMENTS

| | | | |
|---|---|---|---|
| 6,506,153 B1* | 1/2003 | Littek et al. | 600/301 |
| 6,575,902 B1* | 6/2003 | Burton | 600/300 |
| 7,206,631 B2* | 4/2007 | Kawachi et al. | 600/519 |
| 2003/0043045 A1* | 3/2003 | Yasushi et al. | 340/576 |
| 2004/0215265 A1 | 10/2004 | Keizer | |
| 2004/0230104 A1* | 11/2004 | Yanagidaira et al. | 600/300 |
| 2004/0236236 A1* | 11/2004 | Yanagidaira et al. | 600/509 |
| 2006/0004266 A1 | 1/2006 | Shirai et al. | |
| 2006/0155175 A1 | 7/2006 | Ogino et al. | |
| 2007/0123758 A1 | 5/2007 | Miesel et al. | |
| 2008/0071177 A1* | 3/2008 | Yanagidaira et al. | 600/483 |
| 2009/0209829 A1* | 8/2009 | Yanagidaira et al. | 600/301 |
| 2010/0049066 A1 | 2/2010 | Hatakeyama | |

FOREIGN PATENT DOCUMENTS

| | | | |
|---|---|---|---|
| JP | A-08-182667 | 7/1996 | |
| JP | A-11-314534 | 11/1999 | |
| JP | A-2004-290324 | 10/2004 | |
| JP | A-2004-344269 | 12/2004 | |
| JP | A-2005-095408 | 4/2005 | |
| JP | A-2005-342188 | 12/2005 | |
| JP | A-2006-015046 | 1/2006 | |
| JP | A-2007-000280 | 1/2007 | |
| JP | 2008154681 A * | 7/2008 | A61B 5/08 |
| JP | A-2008-161664 | 7/2008 | |
| WO | WO 95/33403 | 12/1995 | |
| WO | WO 2008/069337 A1 | 6/2008 | |

OTHER PUBLICATIONS

Takada, Hajime et al., "Study on Evaluation System of Arousal-level with Physiological Information," Preprints of Meeting on Automotive Engineers, May 2006, No. 4-06, pp. 21-26 (with partial translation).
Atsumi, Bunji, "Evaluation of Mental Condition on Drivers by Analysis of Heart Rate Variability," Preprints of Meeting on Automotive Engineers, Sep. 1994, No. 946, pp. 133-136 (with partial translation).
Yasushi, Mitsuo et al., "Estimation Sleepiness during Expressway Driving," Journal of International Society of Life Information Science, Sep. 2003, vol. 21, No. 2, pp. 445-448 (with translation).
International Search Report issued in International Patent Application No. PCT/JP2010/058904 dated Jun. 29, 2010 (with translation).
Yutaka Yoshida et al., "Analysis of the mental state transition using the heart rate variability", Japan Ergonomics Society, Collection of papers of Tokai-branch conference 2004, pp. 64-65 (with partial translation).
Humin Li et al., "Study on Evaluation System of Arousal-level with Physiological Information" (with partial translation).
Etsunort Fujita et al., "Development of the measurement method of the prediction of sleep by finger plethysmogram data", Journal of Ergonomics 2005, vol. 41, No. 4, pp. 203-212 (with partial translation).
Nov. 27, 2014 Search Report issued in European Patent Application No. 10786066.0.

* cited by examiner

SLEEPINESS ASSESSMENT APPARATUS

TECHNICAL FIELD

The present invention relates to a sleepiness assessment apparatus for determining the degree of sleepiness of a subject.

BACKGROUND ART

Hitherto, an apparatus that detects a sleepy state of a driver in a vehicle has been proposed as this type of sleepiness assessment apparatus (for example, see PTL 1). In this apparatus, by utilizing the fact that activities of the sympathetic nervous system increase in a case where a person is in a state in which the person struggles against sleepiness, a time series of a cardiac cycle is acquired from a cardiac signal detected by a heartbeat sensor. Additionally, the amplitude spectral power of a low-frequency component of heart rate fluctuation is acquired from the time series of the cardiac cycle. When the amplitude spectral power of the low-frequency component of the heart rate fluctuation is larger than a predetermined value, it is determined that the degree of arousal is reduced. Note that, when it is determined that the degree of arousal is reduced, a stimulus, for example, a sound such as a buzzer, light such as meter illumination, or vibration, is applied in order to increase the degree of arousal of the driver.

DISCLOSURE OF INVENTION

As described above, detection of a sleepy state of a driver in a vehicle at an early stage to prevent the driver from falling asleep at the wheel is considered to be a very significant safety issue. However, because there are large differences among individuals in a case of estimating autonomic nervous activities using the above-mentioned heart rate fluctuation, there occur cases in which detection of a sleepy state cannot be stably performed.

It is a main object of a sleepiness assessment apparatus according to the present invention to accurately determine the degree of sleepiness of a person.

The sleepiness assessment apparatus according to the present invention employs the following means in order to achieve the above-mentioned main object.

The sleepiness assessment apparatus according to the present invention is a sleepiness assessment apparatus for determining whether or not a subject is sleepy, the sleepiness assessment apparatus comprising:

a respiration-interval acquisition unit for acquiring a respiration interval of the subject; and a sleepiness assessment unit for determining, in a case where a variation in which the acquired respiration interval increases occurs, by using a degree of the variation as a sleepiness assessment parameter, whether or not the subject is sleepy.

In the sleepiness assessment apparatus according to the present invention, the respiration interval of the subject is acquired, and, in the case where a variation in which the acquired respiration interval increases occurs, whether or not the subject is sleepy is determined by using a degree of the variation as the sleepiness assessment parameter. The sleepiness assessment parameter is based on the fact that, when a person feels sleepy, because the person yawns or breathes deeply more often, the respiration interval varies by a large amount, compared with that in a case where the person is sufficiently awake. Accordingly, whether or not the subject is sleepy can more accurately be determined.

In the above-described sleepiness assessment apparatus according to the present invention, the sleepiness assessment parameter may be a parameter that is, in the case where a variation in which the acquired respiration interval increases occurs, obtained on the basis of a ratio obtained by the variation. In this manner, whether or not the subject is sleepy can be further accurately determined.

Additionally, in the sleepiness assessment apparatus according to the present invention, the sleepiness assessment parameter may be a parameter that is obtained by calculating a standard deviation of the acquired respiration interval. In this manner, whether or not the subject is sleepy can be further accurately determined.

Moreover, in the sleepiness assessment apparatus according to the present invention, the sleepiness assessment parameter may include a plurality of sleepiness assessment parameters, and the sleepiness assessment unit may determine, by using the plurality of sleepiness assessment parameters and weights, each of the weights being set for a corresponding one of the plurality of sleepiness assessment parameters, whether or not the subject is sleepy. In this manner, even when it is supposed that a reaction of a person in a case where the person feels sleepy varies with individuals, whether or not the subject is sleepy can be more accurately determined.

Additionally, the sleepiness assessment apparatus according to the present invention may further include a heartbeat-interval acquisition unit for acquiring a heartbeat interval of the subject. The sleepiness assessment unit may calculate an average value of the acquired heartbeat interval, and determine, in a case where a variation in which the acquired heartbeat interval decreases occurs, by using a frequency of the variation and the calculated average value of the heartbeat interval as the sleepiness assessment parameter, whether or not the subject is sleepy. In the sleepiness assessment apparatus according to this aspect of the present invention, the sleepiness assessment parameter may be a parameter that is, every time a variation in which the acquired heartbeat interval decreases occurs, obtained by multiplying the calculated average value of the heartbeat interval by a value which is obtained by dividing the acquired heartbeat interval by the number of heartbeats per unit time. In this case, the sleepiness assessment parameter may be a parameter that is, every time a variation in which the acquired heartbeat interval decreases occurs, obtained by integrating a square of the calculated average value of the heartbeat interval to obtain an integrated value, and by dividing the integrated value by a unit time.

DESCRIPTION OF PREFERRED EMBODIMENTS

Figure 1:
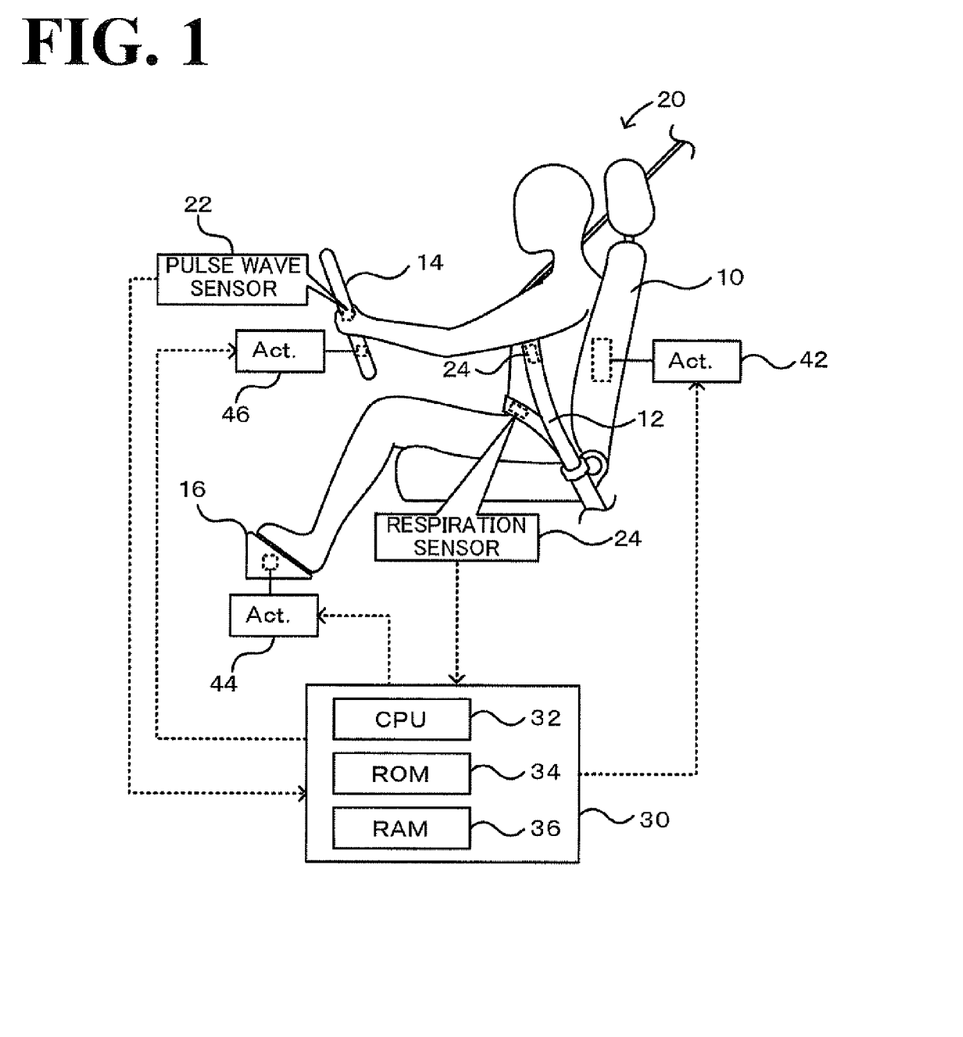
FIG. 1 is a configuration diagram schematically illustrating a configuration of an anti-dozing system including a sleepiness assessment apparatus 20 that is provided as an embodiment of the present invention.

Next, preferred embodiments of the present invention will be described. FIG. 1 is a configuration diagram schematically illustrating a configuration of an anti-dozing system including a sleepiness assessment apparatus 20 that is provided as an embodiment of the present invention. The sleepiness assessment apparatus 20 according to the embodiment is configured as an apparatus that is mounted in an automobile and that is used to determine the degree of sleepiness of a driver. As illustrated in the figure, the sleepiness assessment apparatus 20 includes a pulse wave sensor 22 that detects a pulse wave of the driver, a respiration sensor 24 that detects breathing movement of the driver, and a controller 30 that performs overall control of the apparatus.

Figure 2:
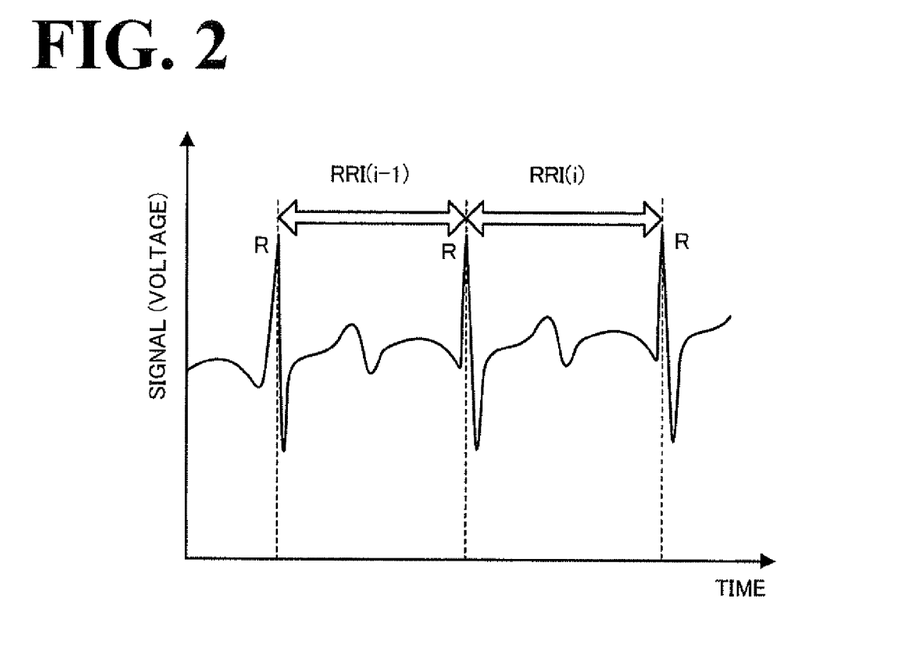
FIG. 2 is an explanatory diagram for explaining a heartbeat interval RRI of an electrocardiogram.

The pulse wave sensor 22 is attached to a grip portion of a steering wheel 14. The pulse wave sensor 22 is an optical sensor that is constituted by a light emitting element which emits near infrared light so that the driver is irradiated with the near infrared light from the skin surface and a light receiving element which receives transmitted light or reflected light. The pulse wave sensor 22 detects, as change in the amount of light, change in the volume flow of blood flowing through peripheral blood vessels. It is considered that a peak-to-peak interval of an acceleration pulse wave which is obtained by a signal detected by the pulse wave sensor 22 corresponds to an interval (heartbeat interval) between R waves of an electrocardiogram illustrated in FIG. 2. The signal detected by the pulse wave sensor 22 is output, in a wireless or wired manner, to the controller 30 via an amplifier and a filter for reducing noise.

Figure 3:
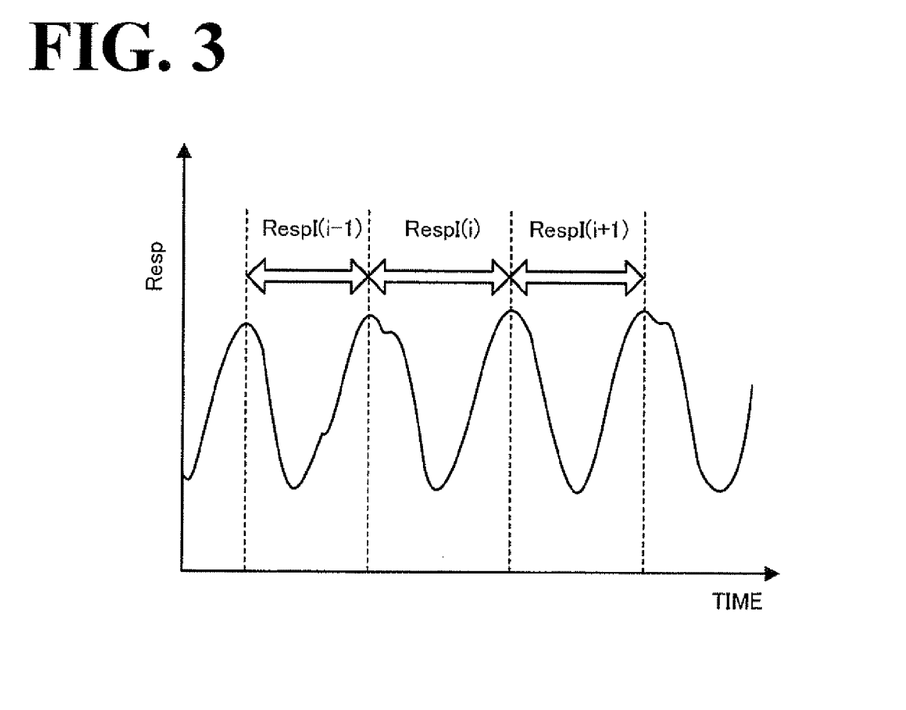
FIG. 3 is an explanatory diagram illustrating an example of a waveform of a signal detected by a respiration sensor 24.

The respiration sensor 24 is a strain gauge that is attached to an area which comes into contact with the thoracicoabdominal part of the driver when a seat belt 12 is fastened. The respiration sensor 24 detects, as change in an electric resistance, movement of the chest or the abdomen of the driver when the driver breathes. In FIG. 3, an example of a waveform of a signal detected by the respiration sensor 24 is illustrated. The signal detected by the respiration sensor 24 is output, in a wireless or wired manner, to the controller 30 via an amplifier and a filter for reducing noise.

The controller 30 is configured as a microprocessor in which a CPU 32 serves as a central unit. In addition to the CPU 32, the controller 30 includes a ROM 34 in which a processing program is stored, a RAM 36 that temporarily stores data, and an input/output port that is not illustrated. The pulse wave signal that is output from the pulse wave sensor 22, the respiration signal that is output from the respiration sensor 24, and so forth are input to the controller 30 via the input port. Furthermore, drive signals that are to be provided to vibration applying actuators (motors) 42, 44, and 46, which are embedded in a backrest portion of a seat 10, a footrest 16, and the steering wheel 14 and which apply vibration, and so forth are output from the controller 30 via the output port.

Figure 4:
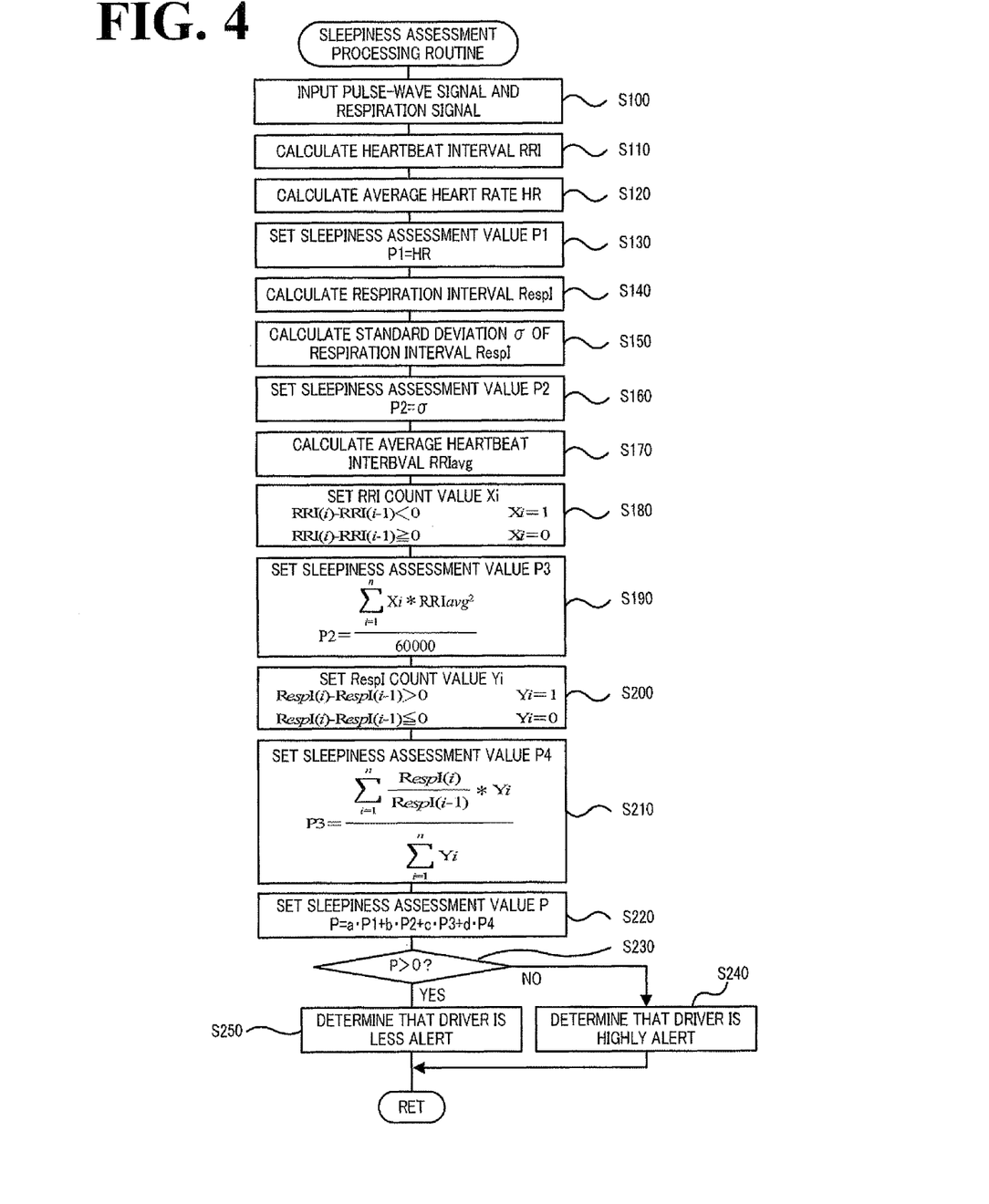
FIG. 4 is a flowchart illustrating an example of a sleepiness assessment processing routine that is performed by a controller 30.

Next, an operation of the sleepiness assessment apparatus 20 having the above-described configuration will be described. FIG. 4 is a flowchart illustrating an example of a sleepiness assessment processing routine that is performed by the controller 30. This routine is repeatedly performed on a predetermined-time-by-predetermined-time basis.

Figure 5:
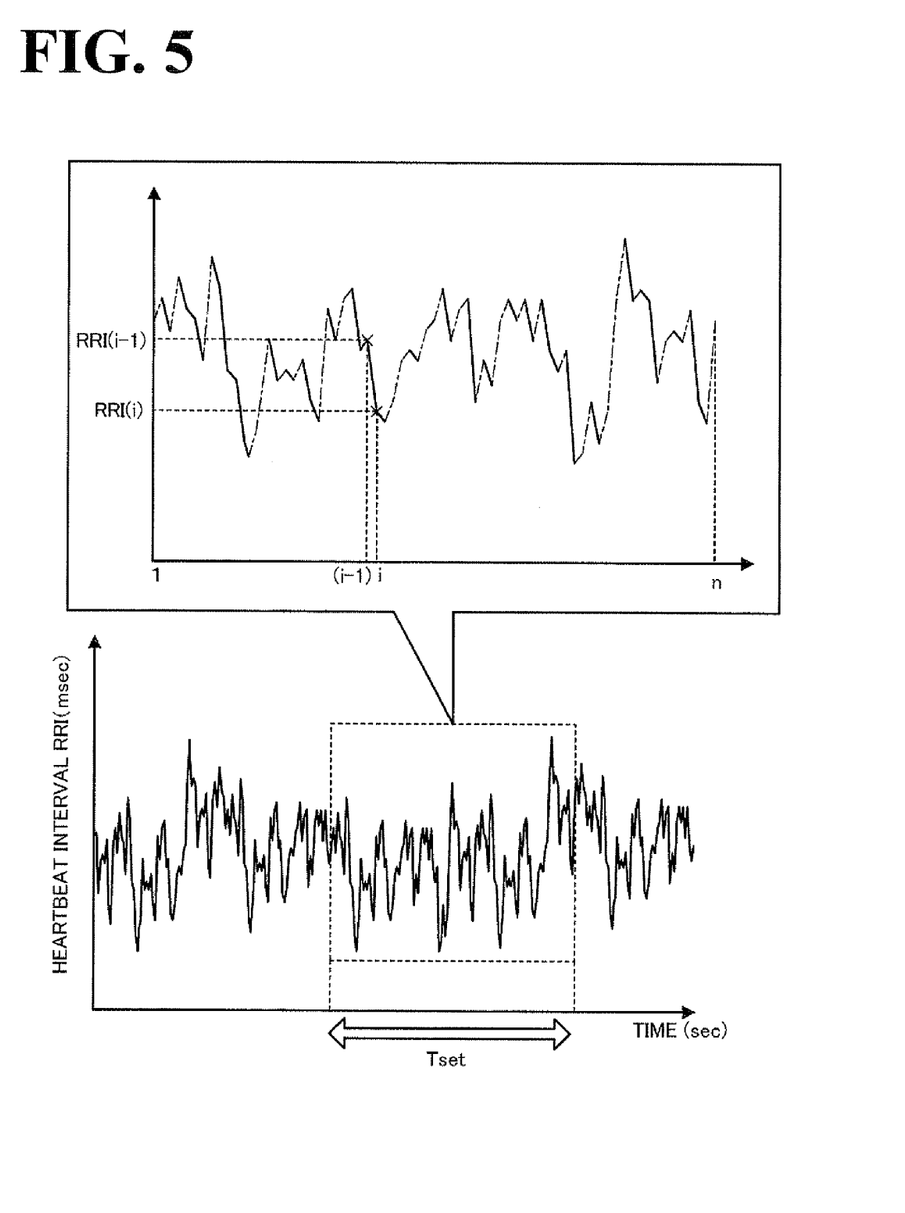
FIG. 5 is an explanatory diagram illustrating an example of a waveform of the heartbeat interval RRI.

When the sleepiness assessment processing routine is performed, first, the CPU 32 of the controller 30 inputs data that is necessary for processing, such as the pulse wave signal that is output from the pulse wave sensor 22 and the respiration signal that is output from the respiration sensor 24 (step S100). Then, the CPU 32 extracts a peak (a maximal value) of the input pulse wave signal, and calculates, as a heartbeat interval RRI, the time difference between a currently extracted peak and the peak extracted immediately prior to the currently extracted peak (step S110). An example of a waveform of the heartbeat interval RRI is illustrated in FIG. 5.

Then, the CPU 32 calculates an average heart rate HR (times/min) for one minute (60000 msec) by using Equation (1), which is given below, on the basis of the calculated heartbeat interval RRI (step S120), and sets a sleepiness assessment value P1 to be the calculated average heart rate HR (step S130). Here, the sleepiness assessment value P1 is one of parameters for determining whether or not the driver is sleepy, and is based on the fact that, in a situation in which a person cannot fall asleep, such as during driving, because the person is consciously trying to remain awake, the heart rate shows a tendency to temporarily increase.

$$HR = 60000/RRI \quad (1)$$

Figure 6:
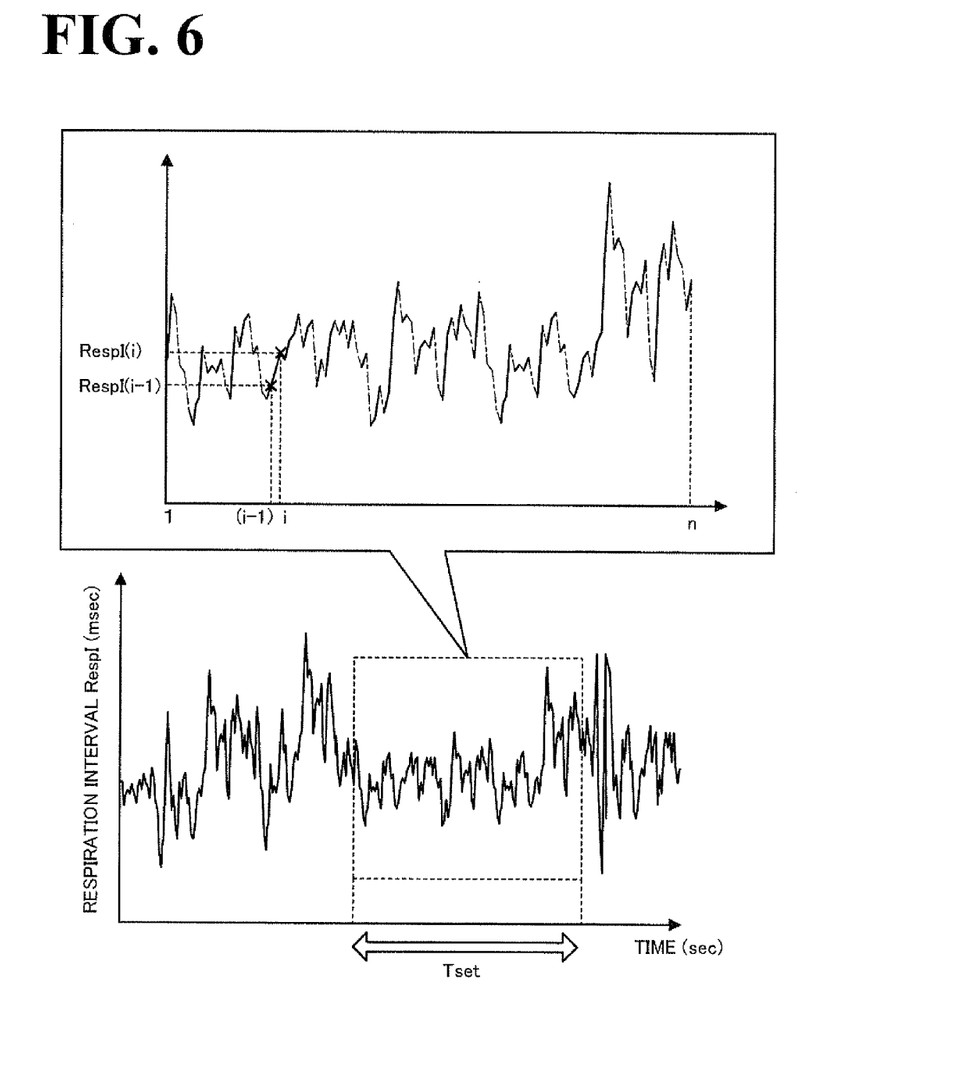
FIG. 6 is an explanatory diagram illustrating an example of a waveform of a respiration interval RespI.

When the CPU 32 sets the sleepiness assessment value P1, next, the CPU 32 extracts a peak (a maximal value) of the input respiration signal, and calculates, as a respiration interval RespI, the time difference between a currently extracted peak and the peak extracted immediately prior to the currently extracted peak (step S140). An example of a waveform of the respiration interval RespI is illustrated in FIG. 6. Then, the CPU 32 computes a standard deviation σ of the calculated respiration interval RespI for one minute (step S150). The CPU 32 sets a sleepiness assessment value P2 to be the computed standard deviation σ of the respiration interval RespI (step S160). Here, the sleepiness assessment value P2 is one of the parameters for determining whether or not the driver is sleepy, and is based on the fact that, when a person feels sleepy, because the person yawns or breathes deeply more often, a large variation occurs in the respiration interval RespI, compared with that in a case where the person is sufficiently awake.

When the CPU 32 sets the sleepiness assessment value P2, the CPU 32 calculates an average heartbeat interval RRIavg from the heartbeat interval RRI, which has been calculated in step S110, by using Equation (2) given below (step S170), and sets an RRI count value Xi by using Equation (3) given below (step S180). The CPU 32 sets a sleepiness assessment value P3 on the basis of the set RRI count value Xi and the average heartbeat interval RRIavg by using Equation (4) given below (step S190). Here, "n" in Equation (2) denotes the number of heartbeats per minute. Furthermore, as represented by Equation (3), when, for one minute, a heartbeat interval RRI (i) that is currently calculated is smaller than a heartbeat interval RRI (i−1) that was calculated immediately prior to the heartbeat interval RRI (i), the RRI count value Xi is incremented by a value of one (see FIG. 5). The sleepiness assessment value P3 is based on the fact that many examples are confirmed, in which, when a person feels sleepy, because a variation in which the heartbeat interval decreases frequently occurs, the frequency of the variation shows a tendency to gradually increase.

$$RRIavg = \frac{1}{n}\sum_{i=1}^{n} RRI(i) \quad (2)$$

$$\begin{aligned} RRI(i) - RRI(i-1) &< 0 \quad Xi = 1 \\ RRI(i) - RRI(i-1) &\geq 0 \quad Xi = 0 \end{aligned} \quad (3)$$

$$P3 = \frac{\sum_{i=1}^{n} Xi * RRIavg^2}{60000} \quad (4)$$

When the CPU 32 sets the sleepiness assessment value P3, the CPU 32 sets a RespI count value Yi by using Equation (5) given below (step S200), and sets a sleepiness assessment value P4 on the basis of the set RespI count value Yi by using Equation (6) given below (step S210). Here, as represented by Equation (5), when, for one minute, a respiration interval RespI (i) that is currently calculated is larger than a respiration interval RespI (i−1) that was calculated immediately prior to the respiration interval RespI (i), the RespI count value Yi is incremented by a value of one (see FIG. 6). As is clear from Equation (6), the sleepiness assessment value P4 is a value obtained by averaging a variation ratio in a case where a variation in which the respiration interval RespI increases occurs, and shows a tendency to increase as the frequency of an action of causing longer breathing, such as a deep breath or a yawn, increases.

$$RespI(i) - RespI(i-1) > 0 \quad Yi = 1$$
$$RespI(i) - RespI(i-1) \leq 0 \quad Yi = 0 \quad (5)$$

$$P4 = \frac{\sum_{i=1}^{n} \frac{RespI(i)}{RespI(i-1)} * Yi}{\sum_{i=1}^{n} Yi} \quad (6)$$

When the CPU 32 sets the individual sleepiness assessment values P1 to P4 in this manner, the CPU 32 sums values that are obtained by multiplying the individual sleepiness assessment values P1 to P4 by coefficients a to d, each of which is set in advance for a corresponding one of the sleepiness assessment values P1 to P4, thereby setting a sleepiness assessment value P (step S220). The CPU 32 compares the set sleepiness assessment value P and a value of zero with each other (step S230). When the sleepiness assessment value P is smaller than the value of zero, the CPU 32 determines that the driver is in a state in which the driver does not feel sleepy, i.e., a state in which the driver is highly alert (step S240). When the set sleepiness assessment value P is equal to or larger than the value of zero, the CPU 32 determines that the driver is in a state in which the driver feels sleepy, i.e., a state in which the driver is less alert (step S250). The CPU 32 finishes the present routine. Here, the coefficients a to d are weight coefficients that are set for the sleepiness assessment values P1 to P4, respectively. Specific values of the coefficients a to d may be determined on the basis of experiments or the like. The reason why the sleepiness assessment value P for determining whether or not the driver feels sleepy is set using the multiple sleepiness assessment values P1 to P4 and the coefficients a to d as described above is that, because indicators indicating a reaction of a person in a case where the person feels sleepy vary with individuals, stable determination cannot be performed using single physiological indicator in most cases. Note that, in the embodiment, when it is determined in the sleepiness assessment processing routine that the driver is less alert, the controller 30 controls the vibration applying actuators so as to apply vibration at predetermined time intervals (for example, one-second intervals), thereby applying a stimulus to improve the degree of arousal. As a matter of course, the scheme for applying a stimulus to the driver is not limited to thereto. Various schemes including provision of a sound such as a buzzer, provision of light such as room light, and application of a pressure using an air bag or the like may be employed.

In the sleepiness assessment apparatus 20 according to the embodiment described above, the sleepiness assessment value P4 is set by averaging a variation ratio in a case where a variation in which the respiration interval RespI increases occurs, and whether or not the driver is sleepy is determined using the set sleepiness assessment value P4 as one of the parameters. Thus, whether or not the driver is sleepy can be accurately determined using the indicator indicating the respiratory interval. Additionally, the sleepiness assessment value P is set using the four sleepiness assessment values P1 to P4 and the weights a to d, each of which is set for a corresponding one of the sleepiness assessment values P1 to P4. Thus, even when it is supposed that that indicators indicating a reaction of a person in a case where the person feels sleepy vary with individuals, more stable determination of whether or not the driver is sleepy can be performed. Furthermore, the average heart rate HR is used as the sleepiness assessment value P1. The standard deviation σ of the respiration interval RespI for one minute is used as the sleepiness assessment value P2. A value, per unit time, of the square of the average heartbeat interval RRIavg in a case where the RRI count value Xi is the value of one is used as the sleepiness assessment value P3. Thus, whether or not the driver is sleepy can be more accurately determined.

In the sleepiness assessment apparatus 20 according to the embodiment, determination of whether or not the driver is in the state in which the driver is less alert or the state in which the driver is high alert, i.e., determination using two steps, is performed on the basis of the sleepiness assessment value P. However, determination performed in the sleepiness assessment apparatus 20 is not limited thereto. Determination of the level of arousal using multiple steps that are equal to or more than three steps may be performed, for example, as follows: two thresholds Pref1 and Pref2 are set; when the sleepiness assessment value P is equal to or larger than the threshold Pref1, it is determined that the level of arousal is a high level; when the sleepiness assessment value P is equal to or larger than the threshold Pref2 and smaller than the threshold Pref1, it is determined that the level of arousal is a median level; and when the sleepiness assessment value P is smaller than the threshold Pref2, it is determined that the level of arousal is a low level.

In the sleepiness assessment apparatus 20 according to the embodiment, whether or not the driver is sleepy is determined using the four sleepiness assessment values P1 to P4. However, some of the sleepiness assessment values may be omitted, if at least either the sleepiness assessment value P3 or P4 is included as an indicator regarding variation in the respiration interval RespI. Whether or not the driver is sleepy may be determined using five or more sleepiness assessment values.

In the sleepiness assessment apparatus 20 according to the embodiment, the heartbeat interval RRI is calculated using the pulse wave sensor 22 as a heartbeat sensor. However, the pulse wave sensor 22 is not limited thereto. Any heartbeat sensor may be used if the heartbeat sensor is a sensor that can detect something corresponding to the cardiac signal, for example, a sensor in which an electrode is attached to each of grip portions of the steering wheel 14 on the left and right sides, and which detects a potential difference in a case where both hands are in contact with the electrodes on the left and right sides.

In the sleepiness assessment apparatus 20 according to the embodiment, a strain gauge is used as the respiration sensor 24. However, the respiration sensor 24 is not limited thereto. Any respiration sensor may be used if the respiration sensor is a sensor that can detect breathing movement, for example, a sensor that detects, by using laser ranging, movement of the thoracicoabdominal part which is made along with respiration.

The relationships between main elements in the embodiment and main elements, which are described in Means for Solving the Problems, of the invention will be described. In the embodiment, the respiration sensor 24 and the controller 30 that performs, in step S140 of the sleepiness assessment processing routine, the process of calculating the respiration interval RespI on the basis of the respiration signal that is output from the respiration sensor 24 correspond to "a respiration-interval acquisition unit". The controller 30 that performs, in steps S130, S150, and S160 to S250, the process of setting the sleepiness assessment value P4 by averaging the variation ratio in the case where a variation in which the respiration interval RespI increases occurs, of setting the sleepiness assessment value P using the sleepiness assessment values P1 to P4, which include the set sleepiness assessment value P4, and the weight coefficients a to d, of determining, when the set sleepiness assessment value P is smaller than the value of zero, that the driver is highly alert, and of determining, when the sleepiness assessment value P is equal to or larger than the value of zero, that the driver is less alert corresponds to "a sleepiness assessment unit". Furthermore, the controller 30 that performs, in step S110, the process of calculating the heartbeat interval RRI on the basis of the pulse wave signal which is output from the pulse wave sensor 22 and the pulse wave sensor 22 corresponds to "a heartbeat-interval acquisition unit".

The embodiments of the present invention are described above. However, the present invention is not limited to the above-described embodiments at all. As a matter of course, various modifications may be made without departing from the gist of the present invention.

The present application claims priority on the basis of Japanese Patent Application No. 2009-137551 filed on Jun. 8, 2009. The entire contents of the application noted above are hereby incorporated by reference.

INDUSTRIAL APPLICABILITY

The present invention may be utilized in industries for producing sleepiness assessment apparatuses, automobile industries, and so forth.

The invention claimed is:

1. A sleepiness assessment apparatus for determining whether or not a subject is sleepy, the sleepiness assessment apparatus comprising:
 a respiration-interval acquisition unit configured to acquire a plurality of respiration intervals of the subject;
 a heartbeat-interval acquisition unit configured to acquire a plurality of heartbeat intervals of the subject;
 a sleepiness assessment unit configured to:
  determine whether a variation occurs in which the acquired respiration intervals increase, calculate a degree of the variation in a case where the variation occurs, and set a first sleepiness parameter based on the calculated degree of the variation,
  calculate an average value of the plurality of acquired heartbeat intervals, determine whether a variation occurs in which the acquired heartbeat intervals decrease, calculate a frequency of the variation in a case where the variation occurs and set a second sleepiness assessment parameter based on the calculated frequency of the variation and the calculated average value of the heartbeat intervals, and
  determine whether or not the subject is sleepy based on the first sleepiness assessment parameter and the second sleepiness assessment parameter; and
 an actuator configured to apply a stimulus to the subject for improving the subject's degree of arousal based on whether or not the subject is sleepy.

2. The sleepiness assessment apparatus according to claim 1,
 wherein the sleepiness assessment unit is configured to, in the case where the variation occurs in which the acquired respiration intervals increase, calculate a ratio of the variation, and set the first sleepiness assessment parameter based on the calculated ratio obtained by the variation.

3. The sleepiness assessment apparatus according to claim 1,
 wherein the sleepiness assessment unit is configured to set a third sleepiness assessment parameter based on a standard deviation of the acquired respiration intervals, and is configured to determine whether or not the subject is sleepy based on the first sleepiness assessment parameter, the second sleepiness assessment parameter, and the third sleepiness assessment parameter.

4. The sleepiness assessment apparatus according to claim 1,
 wherein the sleepiness assessment parameter includes a plurality of sleepiness assessment parameters, and the sleepiness assessment unit determines, by using the plurality of sleepiness assessment parameters and weights, whether or not the subject is sleepy, each of the weights being set for a corresponding one of the plurality of sleepiness assessment parameters.

5. The sleepiness assessment apparatus according to claim 1,
 wherein the sleepiness assessment unit is configured to set the second sleepiness assessment parameter based on the calculated frequency of the variation and the calculated average value of the heartbeat intervals by integrating the calculated average value of the heartbeat intervals every time the variation occurs in which the acquired heartbeat intervals decrease and dividing the integrated value by the number of heartbeats per unit time.

6. The sleepiness assessment apparatus according to claim 5,
 wherein the sleepiness assessment unit is configured to set the second sleepiness assessment parameter based on the calculated frequency of the variation and the calculated average value of the heartbeat intervals by integrating a square of the calculated average value of the heartbeat intervals to obtain an integrated value every time the variation occurs in which the acquired heartbeat intervals decrease, and dividing the integrated value by a unit time.

* * * * *